United States Patent [19]

Mallams et al.

[11] 4,066,752
[45] Jan. 3, 1978

[54] 1-DESAMINO-1-HYDROXY AND 1-DESAMINO-1-EPI-HYDROXY-4,6-DI-O-(AMINOGLYCOSYL)-1,3-DIAMINOCYCLITOLS; 1-DESAMINO-1-OXO-4,6-DI-O-(AMINOGLYCOSYL)-1,3-DIAMINOCYCLITOLS, INTERMEDIATES AND USE AS ANTIBACTERIAL AGENTS

[75] Inventors: Alan K. Mallams, West Orange, N.J.; David Huw Davies, Macclesfield, England

[73] Assignee: Schering Corporation, Kenilworth, N.J.

[21] Appl. No.: 697,804

[22] Filed: June 21, 1976

[51] Int. Cl.$^2$ .................... A61K 31/71; C07H 15/22
[52] U.S. Cl. ........................... 424/180; 536/4; 536/10; 536/17; 536/18

[58] Field of Search ................ 536/17, 4; 424/180

[56] References Cited
U.S. PATENT DOCUMENTS

| 3,828,021 | 8/1974 | Beattie et al. | 536/17 |
| 3,868,360 | 2/1975 | Daniels et al. | 536/17 |
| 3,920,628 | 11/1975 | Daniels | 536/17 |

Primary Examiner—Johnnie R. Brown
Attorney, Agent, or Firm—Elizabeth A. Bellamy; Mary S. King; Stephen B. Coan

[57] ABSTRACT

This invention relates to the preparation of novel 1-desamino-1-oxo-aminoglycosides and their use as intermediates in the preparation of novel 1-desamino-1-hydroxy and 1-desamino-1-epi-hydroxyaminoglycoside antibacterial agents.

20 Claims, No Drawings

1-DESAMINO-1-HYDROXY AND 1-DESAMINO-1-EPI-HYDROXY-4,6-DI-O-(AMINOGLYCOSYL)-1,3-DIAMINOCYCLITOLS; 1-DESAMINO-1-OXO-4,6-DI-O-(AMINOGLYCOSYL)-1,3-DIAMINOCYCLITOLS, INTERMEDIATES AND USE AS ANTIBACTERIAL AGENTS

FIELD OF THE INVENTION

This invention relates to novel compositions of matter to methods for their manufacture and methods for their use as antibacterial agents.

Specifically, this invention relates to novel 1-desamino-1-oxo-4,6-di-O-(aminoglycosyl)-1,3-diaminocyclitols and their use as intermediates in the preparation of novel 1-desamino-1-hydroxy and 1-desamino-1-epi-hydroxy-4,6-di-O-(aminoglycosyl)-1,3-diaminocyclitols useful as antibacterial agents. Further, this invention relates to pharmaceutical compositions comprising said 1-desamino-1-hydroxy and 1-desamino-1-epi-hydroxy derivatives, to methods for their manufacture, and to methods for their use in treating bacterial infections.

Particularly, this invention relates to 1-desamino-1-hydroxy and 1-desamino-1-epi-hydroxy derivatives of 4-O-aminoglycosyl-6-O-garosaminyl-1,3-diaminocyclitol antibiotics including certain gentamicins, sisomicin, verdamicin, Antibiotics G-418, G-52, JI-20A, JI-20B, the 5-epi, 5-epi-azido-5-deoxy, 5-epi-amino-5-deoxy analogs of the foregoing; and Antibiotics Mu-1, Mu-2, Mu-4 and Mu-5.

GENERAL DESCRIPTION OF THE INVENTION

COMPOSITION OF MATTER ASPECT

One composition-of-matter aspect of this invention relates to 1-desamino-1-oxo-derivatives of 4,6-di-O-(aminoglycosyl)-1,3-diaminocyclitols including gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, kanamycin A, kanamycin B, 3', 4'-dideoxykanamycin B, sisomicin, tobramycin, verdamicin, Antibiotics JI-20A, JI-20B, G-52, G-418, 66-40B, 66-40D; the 5-epi, 5-epi-azido-5-deoxy and 5-epi-amino-5-deoxy analogs of the foregoing; and Antibiotics Mu-1, Mu-2, Mu-4 and Mu-5.

The foregoing 1-desamino-1-oxo-4,6-di-O-(aminoglycosyl)-1,3-diaminocyclitols are useful as intermediates in the preparation of the corresponding 1-desamino-1-hydroxy-and 1-desamino-1-epi-hydroxy-4,6-di-O-(aminoglycosyl)-1,3-diaminocyclitols which exhibit antibacterial activity and which are another composition-of-matter aspect of this invention. Of the 1-desamino-1-hydroxy-and 1-desamino-1-epi-hydroxy-4,6-di-O-(aminoglycosyl)-1,3-diaminocyclitols of this invention preferred are those wherein the 6-O-aminoglycosyl unit is 6-O-garosaminyl, including the 1-desamino-1-hydroxy and 1-desamino-1-epi-hydroxy derivatives of gentamicins B, $B_1$, $C_1$, $C_{1a}$, $C_2$, $C_{2a}$, $C_{2b}$, $X_2$, sisomicin, verdamicin, Antibiotics G-52, G-418, JI-20A, JI-20B, the 5-epi, 5-epi-azido-5-deoxy, 5-epi-amino-5-deoxy analogs of the foregoing; and Antibiotics Mu-1, Mu-2, Mu-4 and Mu-5.

Of the foregoing, particularly preferred are those wherein the 1,3-diaminocyclitol is 2-deoxystreptamine, i. e., 1-desamino-1-hydroxy- and 1-desamino-1-epi-hydroxy-derivatives of 4-O-(aminoglycosyl)-6-O-garosaminyl-2-deoxystreptamines such as getamicins B, $B_1$, $C_1$, $C_{1a}$, $C_2$, $C_{2a}$, $C_{2b}$, $X_2$, sisomicin, verdamicin and Antibiotics G-52, G-418, JI-20A and JI-20B. Particularly valuable compounds of the foregoing are 1-desamino-1-hydroxysisomicin, 1-desamino-1-epi-hydroxysisomicin, 1-desamino-1-hydroxygentamicins $C_1$ and $C_{1a}$ and 1-desamino-1-epihydroxygentamicins $C_1$ and $C_{1a}$.

Also included within the composition-of-matter aspect of this invention are the pharmaceutically acceptable acid addition salts of the 1-desamino-1-hydroxy- and 1-desamino-1-epi-hydroxy-4,6-di-O-(aminoglycosyl)-1,3-diaminocyclitols described hereinabove, which are made according to known procedures such as by neutralizing the free base with the appropriate acid usually to about pH 5. Included among the pharmaceutically acceptable acid addition salts of this invention are those derived from organic acids such as acetic acid, propionic acid, succinic acid, fumaric acid and maleic acid, or, preferably, from inorganic acids such as hydrochloric, sulfuric phosphoric and hydrobromic. The physical embodiments of the acid addition salts of this invention are characterized by being white solids which are soluble in water, sparingly soluble in most polar organic solvents and insoluble in most non-polar organic solvents.

In general, the microbiological activity of the 1-desamino-1-hydroxy- and 1-desamino-1-epi-hydroxy-4,6-di-O-(aminoglycosyl)-1,3-diaminocyclitols of this invention and their pharmaceutically acceptable acid addition salts is similar to that of the parent compounds both in vitro and in vivo, but advantageously they are less acutely toxic than their precursor aminoglycosides. The 1-desamino-1-hydroxy- and 1-desamino-1-epi-hydroxy-aminoglycosides are broad-spectrum antibacterials active against both gram-negative and gram-positive strains, being particularly active against many pathogenic types of gram-negative bacteria such as E. coli, Klebsiella, Serratia and Pseudomonas.

PROCESS ASPECT OF THE INVENTION

The invention sought to be patented in its process aspect is the preparation of a compound selected from the group consisting of a 1-desamino-1-hydroxy-, or a 1-desamino-1-epihydroxy-derivative of a 4,6-di-O-(aminoglycosyl)-1,3-diaminocyclitol. This process comprises reacting a 4,6-di-O-(aminoglycosyl)-1,3-diaminocyclitol having an unsubstituted primary amino group at position 1 and all other primary amino groups protected with an amino "protecting" (synonomous with "blocking") group R, with an oxidative deaminating agent. The thereby formed 1-imine derivative is reacted in situ with aqueous acid in the range of pH 1-5. The then formed 1-desamino-1-oxo-poly-N-R-4,6-di-O-(aminoglycosyl)-1,3-diaminocyclitol intermediate of this invention is isolated and further reacted with a hydride donor reducing agent, followed by removal of the N-R blocking groups. Thus, there is produced a product mixture comprising the 1-desamino-1-hydroxy-4,6-di-O-(aminoglycosyl)-1,3-diaminocyclitol and the 1-desamino-1-epi-hydroxy-4,6-di-O-(aminoglycosyl)-1,3-diaminocyclitol which is separated, usually utilizing chromatographic techniques.

Our instant invention deals with a novel process in the aminoglycoside chemistry art. That is, the generation of carbonyl compounds by the efficient oxidative deamination of primary amines. Hitherto, the most commonly employed deamination procedures used on sugars and cyclitols involve nitrosation of the amino group which can lead to ring contraction and unwanted side products.

The conversion of primary amines to carbonyl compounds by the formation of an imine with subsequent transamination involving prototropic interconversion of Schiff bases has not been applied to the aminoglycoside art prior to our invention. By virtue of this transamination technique, a carbonyl compound thus formed can be converted to a hydroxy, or an epi-hydroxy derivative at a hitherto non-oxygenated position in the aminoglycoside molecule, in this case, on position 1 of the 1,3-diaminocyclitol moiety.

In our process it is necessary to "block", or "protect" any primary amino groups other than the 1-amino group on the starting aminoglycoside although secondary amino groups may also be protected. The terms "blocking" group and "protecting" group are used synonymously and each are art recognized terms as being amino derivatives which temporarily "block", or "protect" an amino function in the aminoglycoside molecule from undergoing chemical reactions, yet which are readily removable after a desired chemical reaction is effected at another site on the molecule.

Amino-protecting groups defined as "R" which are useful in our process include acetyl, trifluoroacetyl, trichloroethoxycarbonyl, benzoyl, benzyloxycarbonyl and ethoxycarbonyl. The choice of protecting groups used in our process is dependent upon the amino groups being protected, the reaction conditions and the method desired for removing, or deblocking said groups. This choice is within the knowledge of one skilled in the aminoglycoside art.

As discussed hereinabove, in carrying out our process it is necessary only to "block", or "protect" any primary amino groups in the aminoglycoside molecule other than the 1-amino group. In some cases, in order to increase the stability of the 1-desamino-1-oxo-derivatives of the blocked aminoglycosides, it may be desirable to also protect any secondary amino groups in the molecule. For example, gentamicin $C_{1a}$ can be protected not only at the 3,2' and 6'-positions, but also at the 3"-position. In one mode of carrying out our process (as illustrated in the Preparations and Examples), a trichloroethoxycarbonyl group is used to block the 3,2' and 6'-primary amino groups and an acetyl group is used to block the secondary amino group at the 3"-position. Alternatively, a tetra-N-acetyl derivative could also be used in our process. It is also possible to protect secondary amino groups by virtue of the blocking procedure used. For example, in the acetylation method of Preparation III B, Antibiotic G-52 is automatically acetylated at the secondary amino group at position-6'. However, this blocking at 6'- is not necessary for the further utilization of Antibiotic G-52 in the process.

The following Reaction Scheme is illustrative of our process wherein "R" is an amino protecting group, (A') is the 4-O-aminoglycosyl moiety and (A") is the 6-O-aminoglycosyl-moiety. Ring "D" is the 1,3-diaminocyclitol which optionally may have other groups present, and the oxidation reagent shown is 3,5-di-t-butyl-1,2-benzoquinone:

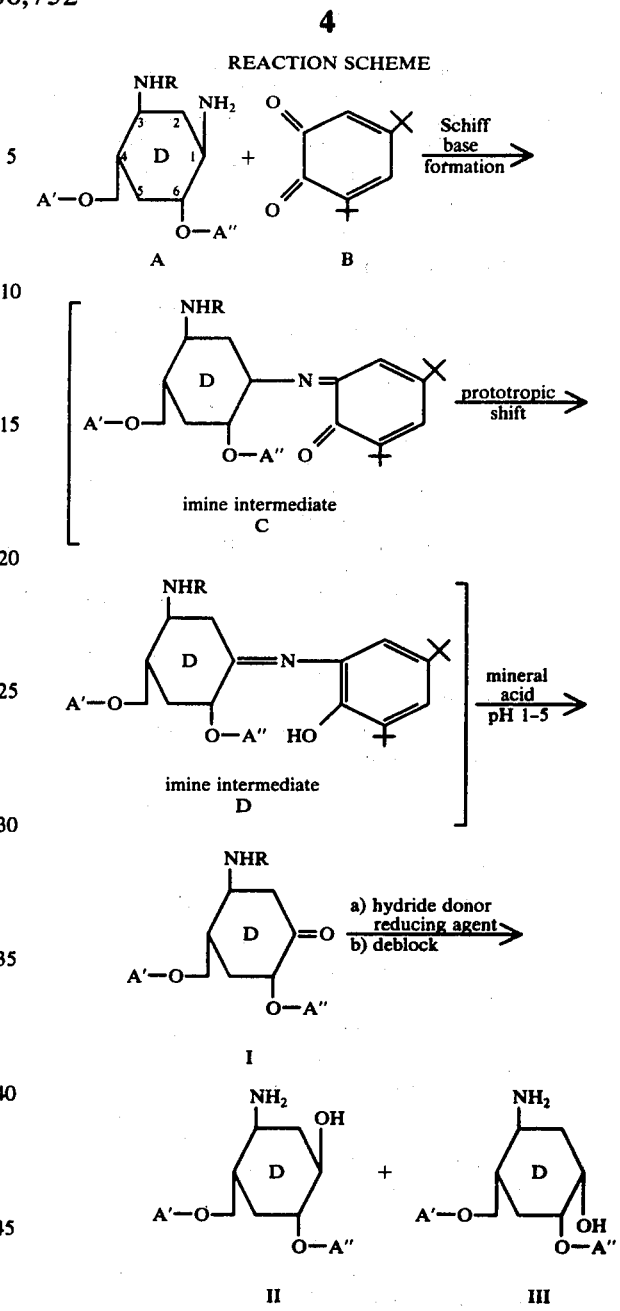

The starting compounds, A, are known 4,6-di-O-(aminoglycosyl)-1,3-diaminocyclitols having antibacterial activity wherein at least all primary amino groups other than the 1-amino function are blocked with an amino protecting group, R, as defined hereinabove. Reaction of A with a mild oxidative deaminating agent, B (preferably 3,5-di-t-butyl-1,2-benzoquinone), produces an imine intermediate, C, in situ, which undergoes a prototropic shift to give the imine intermediate, D. Said imine, upon treatment with an aqueous mineral acid, usually sulfuric acid, or an aqueous organic acid, usually oxalic acid, in the pH range of 1-5 produces 1-desamino-1-oxo-poly-N-R-4,6-di-O-(aminoglycosyl)-1,3-diaminocyclitol intermediates, I, which are novel compounds and are one composition-of-matter aspect of our invention.

Mild oxidative deaminating agents which may be used are those which will form the requisite imine derivative, D, via prototropic shift in situ, from the 1- amino function of the starting blocked aminoglycoside A. Illustrative of such mild oxidative deaminating agents are 3,5-di-t-butyl-1,2-benzoquinone, mesitylglyoxal, 3-nitromesitylglyoxal, 3,5-dinitromesitylglyoxal, benzothiazole-2-carbaldehyde, 6-nitrobenzothiazole-2-carbaldehyde and 2-pyridine carboxaldehyde.

In carrying out our process we usually use 3,5-di-t-butyl-1,2-benzoquinone as the oxidizing agent in a 1:1 molar ratio with respect to the starting aminoglycoside and carry out the reaction at ambient temperatures in a solvent system compatible with the solubility characteristics of the N-R blocking groups which are known to those skilled in the art. For example, if acetyl, or trifluoroacetyl are used as blocking groups, the solvent system is preferably a mixture of methanol-water; whereas, when using trichloroethoxycarbonyl blocking groups which are insoluble in water, an organic solvent such as methanol, or tetrahydrofuran is utilized. The oxidation is carried out until the 1-amino starting compound is consumed as determined by thin layer chromatography, usually about 1 to 24 hours. The 1-imine intermediate, D, thereby formed is then reacted in situ with an aqueous mineral acid, preferably sulfuric acid, or an aqueous organic acid, preferably oxalic acid, in the pH range of 1-5 to form a 1-desamino-1-oxo-poly-N-R-4,69-di-O-(aminoglycosyl)-1,3-diaminocyclitol, (I). Said compound may be isolated as such or, when secondary amino functions are available in the molecule, as the mineral acid addition salt (e.g. sulfate).

The 1-desamino-1-oxo-poly-N-R-aminoglycoside is then reacted in a suitable solvent with an appropriate hydride donor reducing agent. The amino protecting groups in the resulting reduced product may then be deblocked utilizing conventional techniques to produce a mixture of the 1-desamino-1-hydroxy-4,6-di-O-(aminoglycosyl)-1,3-diaminocyclitol (II) and the 1-desamino-1-epi-hydroxy-4,6-di-O-(aminoglycosyl)-1,3-diaminocyclitol, (III). Utilizing chromatographic techniques dependent on the initial starting materials, the foregoing mixture is then separated into its component parts, i. e., the 1-desamino-1-hydroxy-aminoglycoside and the 1-desamino-1-epi-hydroxy-aminoglycoside, novel antibacterial agents of this invention.

The choice of hydride-donor reducing agents utilized in our process is dependent upon the particular starting aminoglycoside. For example, those aminoglycosides which contain unsaturation, e. g. sisomicin, verdamicin, Antibiotic G-52, 66-40B, 66-40D, Mu-1, Mu-2, Mu-4, Mu-5, require the use of a reducing agent which will not destroy the double bond, e. g. sodium cyanoborohydride, sodium borohydride, morpholinoborane, N,N-diethylanilinoborane, and stereoselective trialkylborohydrides such as K-selectride ® and L-selectride ®. Aminoglycoside starting compounds of our process devoid of unsaturations may be reduced with any of the above reagents as well as with diborane and the steroselective trialkylborohydride 9-BBN ®.

The solvents used in this reduction and the pH of the reaction mixture will be dependent on the solubility and stability of the 1-desamino-1-oxo-poly-N-R-blocked aminoglycoside and the particular hydride-donor reducing agent being employed. For example, when utilizing an acetyl blocked aminoglycoside and sodium cyanoborohydride, the reaction is carried out in water at about pH 5; when utilizing a benzoyl blocked aminoglycoside and K-selectride ® as reducing agent the reaction is carried out in tetrahydrofuran at a pH about 10.

The invention described hereinabove is illustrated in detail hereinbelow in the Preparations and Examples which should not be construed as limiting the scope of our invention.

PREPARATION OF INTERMEDIATES

Preparation I

N-(2,2,2-Trichloroethoxycarbonyloxy) succinimide

Dissolve 5.75 gm. of N-hydroxysuccinimide in 200 ml. ethyl acetate and 4 gm. of pyridine; cool the resultant solution to 0° C. To this solution add 10.6 gm. 2,2,2-trichloroethylchloroformate dropwise over a period of 1.5 hours. Filter the resultant mixture and evaporate the filtrate to dryness. Wash the thereby formed needles with hexane to obtain N-(2,2,2-trichloroethoxycarbonyloxy) succinimide, mp. 98°–101° C; $\nu$max (CHCl$_3$) 1825, 1790, 1750, 1185, 826 cm.$^{-1}$, $\delta$(CDCl$_3$) 2.85 (4H,s,—CO (C$\underline{H}_2$)$_2$ CO—) and 4.90 ppm. (2H,s,—COOCH$_2$CCl$_3$).

1-N-Unprotected-Poly-N-Protected-4,6-Di-O-(Aminoglycosyl)-1,3,-Diaminocyclitols

Preparation II

A. 3,2'-Di-N-trifluoroacetylgentamicin C$_1$

Dissolve 35 gm. of gentamicin C$_1$ in 650 ml. of methanol. To the mixture add at room temperature, a solution of 21.2 ml. of ethyl trifluorothiolacetate in 40 ml. of methanol. Stir the reaction mixture for 64 hours. Flush the solution with nitrogen. Concentrate the solution to a residue in vacuo. Chromatograph the residue on 1600 gms. of silica gel G using ammonia saturated methanol and chloroform (2:3). Combine the like fractions as determined by thin layer chromatography and concentrate to obtain 3,2'-di-N-trifluoroacetylgentamicin C$_1$, [$\alpha$]$_D^{26}$ + 121° (H$_2$O); m. p. = 121°–129° C.

B. Poly-N-trifluoroacetyl-4,6-di-O-(aminoglycosyl)-1,3-diaminocyclitols

In a manner similar to that described in Preparation II A. by utilizing as starting compounds:
gentamicin A,
gentamicin B,
gentamicin B$_1$,
gentamicin C$_{2b}$,
gentamicin X$_2$,
Antibiotic G-148,
Antibiotic JI-20A,
Antibiotic JI-20B,
kanamycin B,
the 5-epi, 5-epi-azido-5-deoxy, and 5-epi-amino-5-deoxy analogs of the foregoing and of gentamicin C$_1$; there is obtained, respectively:
3,2'-di-N-trifluoroacetylgentamicin A,
3,4'-di-N-trifluoroacetylgentamicin B$_1$,
3,6'-di-N-trifluoroacetylgentamicin B$_1$,
3,2'-di-N-trifluoroacetylgentamicin C$_{2b}$,
3,2'-di-N-trifluoroacetylgentamicin X$_2$,
3,2'-di-N-trifluoroacetyl Antibiotic G-418,
b 3,2',6'-tri-N-trifluoroacetyl Antibiotic JI-20A,
3,2',6'-tri-N-trifluoroacetyl Antibiotic JI-20B,
3,2',6',3''-tetra-N-trifluoroacetylkanamycin B, and the 5-epi, 5-epi-azido-5-deoxy, 5-epi-amino-5-deoxy analogs of the foregoing and of 3,2'-di-N-trifluoroacetylgentamicin $C_1$.

Preparation III

A. 3,2',6'-Tri-N-acetylsisomicin

Add cupric acetate hydrate (9 gms., 45 mmol) to a stirred solution of sisomicin (1.3 gms., 2.9 mmol) in water (16 ml.) and dimethylformamide (54 ml.). Stir at room temperature for 35 minutes, then to the cupric salt complex thereby formed add dropwise at a rate of about 25 drops per minute 9.3 ml. of a 1 molar solution of acetic anhydride in dimethylformamide (9.3 mmol). Stir the reaction mixture for an additional 30 minutes, then add 30 ml. of water and bubble hydrogen sulfide through the solution for about 10 minutes, stir the mixture for an additional 30 minutes, then filter the solution through a pad of Celite and wash the cupric sulfide residue with three 20 ml. portions of water. Concentrate the combined filtrate and water washings and chromatograph the resultant residue on silica gel (150 gms. 60–200 mesh) eluting with chloroform-methanol-ammonium hydroxide (30:10:1). Combine like fractions as determined by thin layer chromatography and evaporate the fractions containing the major product in vacuo and lyophilize the resultant aqueous mixture to a residue comprising 3,2',6'-tri-N-acetylsisomicin, $[\alpha]_D^{26}$ + 186.7° ($H_2O$); $\delta(D_2O)$ 1.22 (3H,s,4''-$\underline{CH}_3$), 1.94; 1.98; 2.00 (9H,s,N-Ac), 2.51 (3H,s,3''-N-$\underline{CH}_3$), 2.59 (1H, d, $J_2''$, $_3$ ''9.5 Hz, $H_3''$), 5.10 (1H,d,$J_1''$,$_2''$ 4.0 Hz, $H_1''$) and 5.51 ppm. (1H,d,$J_1'$, $_2'$ 2.5 Hz, $H_1'$); m/e 573 [M.+], 443, 425, 415, 397, 392, 374, 364, 346, 233, 215, 211, 205, 187, 160.

B. Poly-N-acetyl-4,6-di-O-(aminoglycosyl)-1,3-diaminocyclitols

In a manner similar to that described in Preparation III A. by utilizing as starting compounds:
verdamicin,
Antibiotic G-52,
Antibiotic 66-40B,
Antibiotic 66-40D,
3',4'-dideoxykanamycin B,
tobramycin,
kanamycin A,
the 5-epi, 5-epi-azido-5-deoxy, 5-epi-amino-5-deoxy analogs of the foregoing and of sisomicin; and
Antibiotic Mu-1,
Antibiotic Mu-2,
Antibiotic Mu-4,
Antibiotic Mu-5,
there is obtained, respectively:
a. 3,2',6'-tri-N-acetylverdamicin,
b. 3,2',6'-tri-N-acetyl Antibiotic G-52,
c. 3,2',6'-tri-N-acetyl Antibiotic 66-40B,
d. 3,2',6'-tri-N-acetyl Antibiotic 66-40D,
e. 3,2',6'-tri-N-acetyl-3',4'-dideoxykanamycin B,
f. 3,2',6'-tri-N-acetyltobramycin,
g. 3,6'-di-N-acetylkanamycin A,
h. the 5-epi, 5-epi-azido-5-deoxy, 5-epi-amino-5deoxy analogs of the foregoing and of 3,2',6'-tri-N-acetylsisomicin; and
i. 3,2',6'-tri-N-acetyl Antibiotic Mu-1,
j. 3,2',6'-tri-N-acetyl Antibiotic Mu-2,
k. 3,2',6'-tri-N-acetyl Antibiotic Mu-4 and
l. 3,5,2',6'-tetra-N-acetyl Antibiotic Mu-5.

Preparation IV

A. 3,2',6'-Tri-N-(2,2,2-trichloroethoxycarbonyl) gentamicin $C_{1a}$

Add cupric acetate hydrate (2.8 gms., 18 mmol) to a stirred solution of gentamicin $C_{1a}$ (1.0 gms., 2 mmol) in dimethylsulfoxide (56 ml.) at 25° C. Continue stirring for 1 hour, then to the cupric salt complex thereby formed add portionwise N-(2,2,2-trichloroethoxycarbonyloxy) succinimide (1.8 gms. 62 mmol) over a 15 minute period. Continue stirring for 2 hours, then dilute the reaction mixture with 2 N ammonium hydroxide (800 ml.) and extract with ethyl acetate (3 × 75 ml.). Evaporate the combined extracts in vacuo and chromatograph the resultant residue on a silica gel column (110 × 2.5 cm.) eluting first with chloroform (250 ml.) and then eluting with chloroform:methanol:concentrated ammonium hydroxide (7:2:0.1 by volume). Combine the like fractions containing the desired product as determined by thin layer chromatography and evaporate the combined fractions to a residue of 3,2',6'-tri-N-(2,2,2-trichloroethoxycarbonyl) gentamicin $C_{1a}$, $[\alpha]_D^{26}$ + 80.0° ($CHCl_3$), $\nu$max (KBr) 3330, 1730, 1520, 1040, 1025 $cm^{-1}$;$\delta(CDCl_3)$ 1.4 (3H, broad s, 4''-$CH_3$), 2.55 (3H, broad s, 3''-$NCH_3$) and 4.64 ppm. (6H, broad s, —NHCOO$\underline{CH}_2CCl_3$).

B. Poly-N-(2,2,2-trichloroethoxycarbonyl)-4,6-di-O-(aminoglycosyl)-1,3-diaminocyclitols In a manner similar to Preparation IV A. by utilizing as starting compounds,
gentamicin $C_2$,
gentamicin $C_{2a}$, and
the 5-epi, 5-epi-azido-5-deoxy, 5-epi-amino-5deoxy analogs of the foregoing and of gentamicin $C_{1a}$, there is obtained, respectively:
3,2',6'-tri-N-(2,2,2-trichloroethoxycarbonyl) gentamicin $C_2$,
3,2',6'-tri-N-(2,2,2-trichloroethoxycarbonyl) gentamicin $C_{2a}$,
and the 5-epi, 5-epi-azido-5-deoxy, 5-epi-amino-5-deoxy analogs of the foregoing and of 3,2',6'-tri-N-(2,2,2-trichloroethoxycarbonyl) gentamicin $C_{1a}$.

Preparation V

A. 3,2',6'-Tri-N-(2,2,2-trichloroethoxycarbonyl)-3''-N-acetyl-gentamicin $C_{1a}$ Dissolve 500 mg. of 3,2',6'-tri-N-(2,2,2-trichloroethoxycarbonyl)-gentamicin $C_{1a}$ from Preparation IV A. in 20 ml. (1:1) tetrahydrofuran and water. Add 84.6 gms. of acetyl imidazole dissolved in 4 ml. tetrahydrofuran. Stir the solution at room temperature for 4 hours. Evaporate the tetrahydrofuran and decant off the remaining water. Dissolve the resultant residue in a small amount of chloroform and wash with water. Evaporate the chloroform and azeotrope the resultant residue with benzene. Chromatograph the azeotroped resultant residue on a silica gel column (30 × 3 cm.) eluting with 10% methanol/chloroform. Combine the fractions to obtain 3,2',6'-tri-N-(2,2,2-trichloroethoxycarbonyl)-3''-N-acetyl gentamicin $C_{1a}$, $[\alpha]_D^{26}$ + 69.9° ($CHCl_3$); $\nu$max (KBr) 1720, 1620 $cm^{-1}$; $\delta$ ($CDCl_3$) 1.08 (3H, s, 4''—$\underline{CH}_3$), 2.16 (3H, s, N-Ac), 3.12 (3H, s, 3''—N—$CH_3$) and 4.76 ppm. (6H, s, $CO_2\underline{CH}_2CCl_3$).

B.
Poly-N-protected-4,6-di-O-(aminoglycosyl)-1,3-diaminocyclitols.

In a manner similar to Preparation V A. by utilizing as starting compounds, 3,2',6'-Tri-N-acetyl-3',4'-dideoxykanamycin B,
3,2',6'-Tri-N-acetyltobramycin,
3,6'-Di-N-acetylkanamycin A, the 5-epi, 5-epi-azido-5-deoxy, 5-epi-amino-5deoxy analogs of the foregoing and of 3,2',6'-tri-N-(2,2,2-trichloroethoxycarbonyl)-3''-N-acetyl gentamicin $C_1a$, there is obtained, respectively:

3,2',6',-3''-tetra-N-acetyl-3',4'-dideoxykanamycin B,
3,2',6',3''-tetra-N-acetyltobramycin,
3,6'-3''-tri-N-acetylkanamycin A, the 5-epi, 5-epi-azido-5-deoxy, 5-epi-amino-5-deoxy analogs of the foregoing and of 3,2',6'-tri-N-(2,2,2-trichloroethoxycarbonyl)-3'-N-acetyl gentamicin $C_1a$.

EXAMPLES

1-Desamino-1-Oxo-Poly-N-Protected-4,6-Di-O-(Aminoglycosyl)-1,3-Diaminocyclitols

EXAMPLE 1

A.
1-Desamino-1-oxo-3,2'-di-N-trifluoroacetylgentamicin $C_1$

To a solution of 3.34 gm. of 3,2'-di-N-trifluoroacetylgentamicin $C_1$ from Preparation II A. in 60 ml. anhydrous methanol add 1.12 gm. 3,5-di-t-butyl-1,2-benzoquinone. Stir the solution at 25° C. under dry nitrogen for 24 hours. Acidify the solution to pH 2.5 to 3.0 with 2N sulfuric acid and continue stirring at 25° C. Follow the hydrolysis by thin layer chromatography, then complete (after about 4 hours), dilute the mixture with water and filter the solids. Extract the aqueous phase with chloroform (2 × 200 ml.) and adjust pH to 6 with Amberlite IRA 401S(OH-) resin. Filter the resin and evaporate the filtrate in vacuo to obtain 1-desamino-1-oxo-3,2'-di-N-trifluoroacetylgentamicin $C_1$ as the sulfate salt, $[\alpha]_D^{26}$ + 129.5° (H₂O); $\nu$ max (KBr) 3200, 1680, 1540, 1100 cm¹; $\delta$(D₂O) 1.21 (3H,d,J7Hz,6'-CH₃), 1.28 (3H,s,4''—CH₃), 2.69 (3H,s,6'—NCH₃) and 2.89 ppm. (3H,s,3''—NCH₃).

B.
1-Desamino-1-oxo-poly-N-trifluoroacetyl-4,6-di-O-(aminoglycosyl)-1,3-diaminocyclitols In a manner similar to Example 1A, treat the products of Preparation II B. with 3,5-di-t-butyl-1,2-benzoquinone in acid media. Isolate and purify each of the resultant products to obtain, respectively:

1-desamino-1-oxo-3,2'-di-N-trifluoroacetylgentamicin A,
1-desamino-1-oxo-3,6'-di-N-trifluoroacetylgentamicin B,
1-desamino-1-oxo-3,6'-di-N-trifluoroacetylgentamicin $B_1$,
1-desamino-1-oxo-3,2'-di-N-trifluoroacetylgentamicin $C_2b$,
1-desamino-1-oxo-3,2'-di-N-trifluoroacetylgentamicin $X_2$,
1-desamino-1-oxo-3,2'-di-N-trifluoroacetyl Antibiotic G-418,
1-desamino-1-oxo-3,2',6'-tri-N-trifluoroacetyl Antibiotic JI-20A,
1-desamino-1-oxo-3,2',6'-tri-N-trifluoroacetyl Antibiotic JI-20B,
1-desamino-1-oxo-3,2',6',3''-tetra-N-trifluoroacetylkanamycin B, and the 5-epi, 5-epi-azido-5-deoxy, 5-epi-amino-5-deoxy analogs of the foregoing and of 1-desamino-1-oxo-3,2'-di-N-trifluoroacetylgentamicin $C_1$.

EXAMPLE 2

A. 1-Desamino-1-oxo-3,2', 6'-tri-N-acetylsisomicin

Dissolve 5 gm. of 3,2', 6'-tri-N-acetylsisomicin from Preparation III A. in 200 ml. anhydrous methanol. To this solution add 1.92 gm. 3,5-di-t-butyl-1,2-benzoquinone and stir under dry nitrogen at 25° C for 25 hours. With 2N sulfuric acid acidify the solution to pH 3, stir the mixture at 25°. C and follow the hydrolysis by thin layer chromatography. When the reaction is complete (i.e. after about 15 hours), dilute the mixture with water and then extract with 3 × 50 ml. chloroform. Neutralize the aqueous layer to pH 7 with 2N ammonium hydroxide and then pass over Amberlite 1R 45 resin. Concentrate the aqueous eluate in vacuo and lyophilize to obtain 1-desamino-1-oxo-3,2', 6'-tri-N-acetylsisomicin, $[\alpha]$ $D^{26}$ + 186.1°(H₂O);$\nu$max (KCl) 3200, 1020 cm⁻¹; $\delta$ (D₂O) 1.30 (3H, s, 4''—CH₃), 1.87, 1.91, 1.96 (9H, s, NHAc) and 2.90 ppm. (3H, s, 3''—NCH₃).

B.
1-Desamino-1-oxo-poly-N-acetyl-4,6-di-O-(aminoglycosyl)-1,3-diaminocyclitols In a manner similar to Example 2A, treat the products (a-d, h, i-l) of Preparation III B. with 3,5-di-t-butyl-1,2-benzoquinone in acid media. Isolate and purify each of the resultant products to obtain, respectively:

1-desamino-1-oxo-3,2', 6' -tri-N-acetylverdamicin,
1-desamino-1-oxo-3,2',6'-tri-N-acetyl Antibiotic G-52,
1-desamino-1-oxo-3,2',6'-tri-N-acetyl Antibiotic 66-40B,
1-desamino-1-oxo-3,2', 6'-tri-N-acetyl Antibiotic 66-40D, the 5-epi, 5-epi-azido-5-deoxy, 5-epi-amino-5-deoxy analogs of the foregoing and of 1-desamino-1-oxo-3,2',6'-tri-N-acetylsisomicin; and 1-desamino-1-oxo-3,2', 6'-tri-N-acetyl Antibiotic Mu-1,
1-desamino-1-oxo-3,2', 6'-tri-N-acetyl Antibiotic Mu-2,
1-desamino-1-oxo-3,2', 6'-tri-N-acetyl Antibiotic Mu-4, and
1-desamino-1-oxo-3,5,2', 6'-tetra-N-acetyl Antibiotic Mu-5.

EXAMPLE 3

A. 1-Desamino-1-oxo-3,2', 6'-tri-N-(2,2,2-trichloroethoxycarbonyl) gentamicin $C_1a$ Dissolve 3.5 gms. 3, 2', 6'-tri-N-(2,2,2-trichloroethoxycarbonyl) gentamicin $C_1$ a from Preparation IV A. in 70 ml. anhydrous methanol. To the solution add 770 mg. 3, 5-di-t-butyl-1,2-benzoquinone and stir at 25° C for 7 hours under nitrogen. Acidify the solution to pH 3 with sulfuric acid and stir the mixture at 25° C for 17 hours. Neutralize the solution to pH 7 with Amberlite IR 45 resin, filter and evaporate the filtrate to dryness. Chromatograph the residue on a silica gel column (20 × 3.5 cm) by gradient elution using chloroform (1.5 L), 1% methanol in chloroform (1 L) and 5% methanol in chloroform (1 L) as the eluant. Evaporate the fractions of the 5% methanol in chloroform eluant to obtain 1-desamino-1-oxo-3,2',6'-tri-N-(2,2,2-trichloroethoxycarbonyl) gentamicin C$_1$a, [α] D$^{26}$ + 86.4° (CHCl$_3$); ν max (KBr) 3425, 3350, 1720, 1520, 1100, 1040 cm.$^{-1}$.

B.
1-Desamino-1-oxo-poly-N-(2,2,2-trichloroethoxycarbonyl)-4,6-di-O-(aminoglycosyl)-1,3-diaminocyclitols:

In a manner similar to Example 3A treat the products of Preparation IV B. with 3,5-di-t-butyl-1,2-benzoquinone. Isolate each of the resultant products to obtain, respectively:
1-desamino-1-oxo-3,2', 6'-tri-N-(2,2,2-trichloroethoxycarbonyl) gentamicin C$_2$,
1-desamino-1-oxo-3,2' 6'-tri-N-(2,2,2-trichloroethoxycarbonyl) gentamicin C$_{2a}$,
and the 5 - epi, 5-epi-azido-5-deoxy, 5-epi-amino-5-deoxy analogs of the foregoing and of 1-desamino-1-oxo-3,2',6'-tri-N-(2,2,2-trichloroethoxycarbonyl) gentamicin C$_1$ a.

EXAMPLE 4

A.
1-Desamino-1-oxo-3,2',6'-tri-N-(2,2,2-trichloroethoxycarbonyl)-3"-N-acetylgentamicin C$_1$ a Dissolve 1 gm. 3,2',6'-tri-N-(2,2,2-trichloroethoxycarbonyl)-3"-N-acetyl gentamicin C$_1$ a from Preparation V A. in 30 ml. anhydrous methanol. To the solution add 216 mg. 3,5-di-t-butyl-1,2-benzoquinone and stir at 25° C for 7 hours under nitrogen. Acidify the solution to pH 3 with sulfuric acid and stir the mixture at 25° C for 17 hours. Neutralize the solution to pH 7 with Amberlite IR 45 resin, filter and evaporate the filtrate to dryness. Chromatograph the residue on a silica gel column (20 × 1.5 cm) by gradient elution using chloroform (1.5 L.), 1% methanol in chloroform (1 L.) followed by 5% methanol in chloroform (1 L.) as the eluant. Evaporate the combined fractions of the 5% methanol in chloroform eluant to obtain 1-desamino-1-oxo-3,2',6'-tri-N-(2,2,2-trichloroethoxycarbonyl)-3"-N-acetyl gentamicin C$_1$ a.

B.
1-Desamino-1-oxo-poly-N-protected-4,6-di-O-(aminoglycosyl)-1,3-diaminocyclitols In a manner similar to Example 4 treat the products of Preparation V B. with 3,5-di-t-butyl-1,2-benzoquinone. Isolate each of the resultant products to obtain, respectively:
1-desamino-1-oxo-3,2',6',3"-tetra-N-acetyl-3',4'-dideoxykanamycin B,
1-desamino-1-oxo-3,2',6',3"-tetra-N-acetyltobramycin,
1-desamino-1-oxo-3,6',3"-tri-N-acetylkanamycin A,
the 5-epi, 5-epi-azido-5-deoxy, 5-epi-amino-5-deoxy analogs of the foregoing and of 1-desamino-1-oxo-3,2',6'-tri-N-(2,2,2-trichloroethoxycarbonyl)-3"-N-acetylgentamicin C$_1$ a.

EXAMPLE 5

A. 1-Desamino-1-hydroxygentamicin C$_1$, and 1-Desamino-1-epi-hydroxygentamicin C$_1$ Dissolve 1 gm. 1-desamino-1-oxo-3,2'-di-N-trifluoroacetylgentamicin C$_1$ (sulfate salt) in 30 ml. water and adjust the pH of the solution to 3 with 1N sulfuric acid. Add 0.6 gm. sodium cyanoborohydride and stir the solution at 25° C for 18 hours. Then add 10 ml. concentrated ammonium hydroxide and stir the solution at 25° C an additional 30 hours. Evaporate the reaction mixture to dryness and chromatograph the residue on a silica gel column (160 × 2.5 cm) using the lower phase of a chloroform-methanol-concentrated ammonium hydroxide solution (2:1:1) as the eluant. Combine like fractions as determined by thin layer chromatography.

a. Combine like fractions containing 1-desamino-1-hydroxygentamicin C$_1$, concentrate, pass over Amberlite IRA 401S (OH—) resin and lyophilize to obtain 1-desamino-1-hydroxygentamicin C$_1$, [α]D$^{26}$ + 154.0° (H$_2$O; ν max (KBr) 3300, 1050 cm$^-$; δ (D$_2$O) 1.00 (3H,d,J7Hz, 6'—CH$_3$), 1.14 (3H,s,4"—CH$_3$), 2.29 (3H,s,6'—NCH$_3$), 2.45 (3H,s,3"—NCH$_3$), 5.09 (1H,d,J$_1$",$_2$' 4Hz,H$_1$")and 5.22 ppm. (1H,d,J$_1$ ',$_2$' 4Hz, H$_1$'); δ c (D$_2$O) 70.8 (C$_1$), 100.5(C$_1$ ") and 102.5 ppm. (C$_1$ '), and b. Combine like fractions containing 1-desamino-1-epi-hydroxygentamicin C$_1$, concentrate, pass over Amberlite IRA 401S(OH—) resin and lyophilize to obtain 1-desamino-1-epi-hydroxygentamicin C$_1$, [α]D$^{26}$ + 164.2° (H$_2$O); δ (D$_2$O) 1.00 (3H,d,J 6.5Hz, 6'—(CH$_3$), 1.15 (3H,s,4"—CH$_3$), 2.29 (3H,s, 6'—NCH$_3$), 2.46 (3H,s,3"—NCH$_3$), 4.25 (1H,m,H$_1$), 5.00 (1H,d,J$_1$ ",$_2$'4Hz,H$_1$") and 5.11 ppm. (1H,d,J$_1$ ',$_2$' 3.5Hz, H$_1$'0; δ c (D$_2$O) 65.3 (C$_1$), 96.7 (C$_1$") and 102.9 ppm. (C$_1$').

B. 1-Desamino-1-hydroxy-and 1-Desamino-1-epi-hydroxy-4,6-di-O-(aminoglycosyl)-1,3-diaminocyclitols In a manner similar to the foregoing, treat the products of Example 1 B with sulfuric acid and sodium cyanoborohydride. Utilize separation techniques as described in Example 5 A to obtain, respectively:
1-desamino-1-hydroxygentamicin A and
1-desamino-1-epi-hydroxygentamicin A,
1-desamino-1-hydroxygentamicin B and
1-desamino-1-epi-hydroxygentamicin B,
1-desamino-1-hydroxygentamicin B$_1$ and
1-desamino-1-epi-hydroxygentamicin B$_1$,
1-desamino-1-hydroxygentamicin C$_2$b and
1-desamino-1-epi-hydroxygentamicin C$_2$b,
1-desamino-1-hydroxygentamicin X$_2$ and
1-desamino-1-epi-hydroxygentamicin X$_2$,
1-desamino-1-hydroxy Antibiotic G-418, and
1-desamino-1-epi-hydroxy Antibiotic G-418
1-desamino-1-hydroxy Antibiotic JI-20A and
1-desamino-1-epi-hydroxy Antibiotic JI-20A,
1-desamino-1-hydroxy Antibiotic JI-20B and
1-desamino-1-epi-hydroxy Antibiotic JI-20B,
1-desamino-1-hydroxykanamycin B
1-desamino-1-epi-hydroxykanamycin B,
and the 5-epi, 5-epi-azido-5-deoxy, 5-epi-amino-5-deoxy analogs of the foregoing and of 1-desamino-1-hydroxygentamicin C$_1$ and 1-desamino-1-epi-hydroxygentamicin C$_1$.

EXAMPLE 6

A. 1-Desamino-1-hydroxysisomicin and 1-desamino-1-epi-hydroxysisomicin

Dissolve 2 gm. of 1-desamino-1-oxo-3,2',6'-tri-N-acetylsisomicin in 100 ml. methanol-water )8:2) and acidify the solution to pH 3 with 2N sulfuric acid. To the solution add 880 mg. of sodium cyanoborohydride and then stir the solution under dry argon for 18 hours at 25° C. Filter the reaction mixture and evaporate the filtrate to dryness in vacuo. Dissolve the residue in 70 ml. 5% aqueous sodium hydroxide and reflux under argon for 60 hours. Cool the solution and neutralize with Amberlite IRC 50 (H+) resin. Wash the resin with water and then elute with 7% ammonium hydroxide solution. Evaporate the basic eluate to dryness and chromatograph the resulting residue on a silica gel column (160 × 2.5 cm.) using the lower phase of a chloroform-methanol-14% ammonium hydroxide solution (2:1:1) as the eluant. Combine like fractions as determined by thin layer chromatography.

a. Combine the less polar fractions containing 1-desamino-1-hydroxysisomicin, concentrate, pass over Amberlite IRA 401S (OH−) resin and lyophilize to obtain 1-desamino-1-hydroxysisomicin, $[\alpha]D^{26}$ + 168.3° (H$_2$O); $\nu$ max (KCl) 3350, 1680, 1000 cm$^{-1}$; $\delta$ (D$_2$O) 1.22 (3H,s, 4″—CH$_3$), 2.52 (3H,s,3″—NCH$_3$), 4.90 (1H,m,H$_4'$), 5.29 (1H, d, $J_1''$,$_2''$ 4Hz,H$_1''$) and 5.38 ppm. (1H,d,$J_1'$,$_2'$ 2Hz, H$_1'$); $\delta$ c (D$_2$O) 71.0 (C$_1$), 100.5 (C$_1''$) and 100.8 ppm. (C$_2'$); and b. Combine the more polar fractions containing 1-desamino-1-epi-hydroxysisomicin and chromatograph on a silica gel column (160 × 2.5 cm.) using a chloroform-methanol-7% ammonium hydroxide solution (1:2:1) as the eluant. Combine the like fractions as determined by thin layer chromatograpy, concentrate, pass over Amberlite IRA 401S (OH−) resin and lyophilize to obtain 1-desamino-1epi-hydroxysisomicin, $[\alpha]D^{26}$ + 145.4° (H$_2$O); $\nu$ max (KBr) 3350, 1680, 1075 cm.$^{-1}$; $\delta$ (D$_2$O) 1.23 (3H, s, 4″—CH$_3$), 2.52 (3H, s, 3″—NCH$_3$), 4.34 (1H, m, H$_1$) 4.91 (1H, m, H$_4'$), 5.08 (1H, d, $J_1''$,$_2''$ 3.5Hz, H$_1''$) and 5.39 ppm. (1H, d, $J_1'$,$_2'$ 2.5Hz, H$_1'$); $\delta$ c (D$_2$O) 65.3 (C$_1$), 96.8 (C$_1''$) and 101.0 ppm. (C$_1'$).

B. 1-Desamino-1-hydroxy and 1-desamino-1-epi-hydroxy-4,6-di-O-(aminoglycosyl)-1,3-diaminocyclitols In a manner similar to the foregoing, treat the products of Example 2 B with sulfuric acid and sodium cyanoborohydride. Utilize separation techniques as described in Example 6 A to obtain, respectively:
1-desamino-1-hydroxyverdamicin and
1-desamino-1-epi-hydroxyverdamicin,
1-desamino-1-hydroxy Antibiotic G-52 and
1-desamino-1-epi-hydroxy Antibiotic G-52,
1-desamino-1-hydroxy Antibiotic 66-40B and
1-desamino-1-epi-hydroxy Antibiotic 66-40B,
1-desamino-1-hydroxy Antibiotic 66-40D and
1-desamino-1-epi-hydroxy Antibiotic 66-40D,
the 5-epi-, 5-epi-azido-5-deoxy, 5-epi-amino-5-deoxy analogs of the foregoing and of 1-desamino-1-hydroxysisomicin and 1-desamino-1-epi-hydroxysisomicin; and
1-desamino-1-hydroxy Antibiotic Mu-1 and
1-desamino-1-epi-hydroxy Antibiotic Mu-1
1-desamino-1-hydroxy Antibiotic Mu-2 and
1-desamino-1-epi-hydroxy Antibiotic Mu-2,
1-desamino-1-hydroxy Antibiotic Mu-4 and
1-desamino-1-epi-hydroxy Antibiotic Mu-4,
1-desamino-1-hydroxy Antibiotic Mu-5 and
1-desamino-1-epi-hydroxy Antibiotic Mu-5.

EXAMPLE 7

A. 1-Desamino-1-hydroxygentamicin C$_1$ a and 1-desamino-1-epi-hydroxygentamicin C$_1$ a 1. Dissolve 1.7 gm. of 1-desamino-1-oxo-3,2′,6′-tri-N-(2,2,2-trichloroethoxycarbonyl) gentamicin C$_1$ a in 50 ml. of methanol and adjust the solution to pH 3 using 2N sulfuric acid. Add 408 mg. sodium cyanoborohydride to the solution and stir at 25° C for 18 hours. Evaporate the reaction mixture to dryness and take up the residue in 50 ml. 10% acetic acid in methanol. Add 428 mg. powdered zinc to the mixture and reflux for 3 hours. Filter the solution, evaporate the filtrate and azeotrope the resultant residue with toluene. Dissolve the resultant solid in water and adjust the pH to 3 by addition of 2N hydrochloric acid. Reconcentrate the solution, azeotrope with toluene and then dissolve the resultant solid in water and pass over Amberlite IRA 401S (OH−) resin. Evaporate the eluate and chromatograph the residue on a silica gel column (160 × 2.5 cm.) using chloroform-methanol-10% ammonium hydroxide solution (1:2:1) as the eluant. Evaporate the eluates and rechromatograph the combined residue on a silica gel column (160 × 2.5 cm.) using the lower phase of a chloroform-methanol-concentrated ammonium hydroxide solution (2:1:1) as the eluant. Combine like fractions as determined by thin layer chromatography.

a. Combine the less polar fractions containing 1-desamino-1-hydroxygentamicin C$_1$a, concentrate, pass over Amberlite IRA 401S (OH−) resin and lyophilize to obtain 1-desamino-1-hydroxygentamicin C$_1$ a, $[\alpha]^D_{26}$ + 150.7° (H$_2$O); $\nu$max (KBr) 3340, 1050 cm. $^{-1}$; $\delta$ (D$_2$O) 1.17 (3H, s, 4″-CH$_3$), 2.50 (3H, s, 3″-NCH$_3$), 5.18 (1H, d, $J_1''$, $_2''$ 4Hz, H$_1''$) and 5.24 ppm. (1H, d, $J_1'$, $_2'$ 3.8Hz, H$_1'$); $\delta$ c (D$_2$O) 69.5 (C$_1$), 100.3 (C$_1''$) and 100.9 ppm. (C$_1'$); and b. Combine the more polar fractions containing 1-desamino-1-epi-hydroxygentamicin C$_1$a, concentrate, pass over Amberlite IRA 401S (OH−) resin and lyophilize to obtain 1-desamino-1-epihydroxygentamicin C$_1$a, $[\alpha]^D_{26}$ + 158.3°(H$_2$O); $\nu$max (KBr) 3350, 1055, 1020 cm.$^{-1}$; $\delta$ (D$_2$O) 1.17 (3H, s, 4″—CH$_3$), 2.50 (3H, s, 3″-NCH$_3$), 4.24 (1H, m, H$_1$), 5.03 (1H, d, $J_1''$, $_2''$ 4Hz, H$_1''$) and 5.20 ppm. (1H, d, $J_1'$, $_2'$ 3.8Hz, H$_1'$); $\delta$ c (D$_2$O) 65.3 (C$_1$), 96.6 (C$_1''$) and 101.9 ppm. (C$_1'$). 2. Dissolve 1.3 gm. of 1-desamino-1-oxo-3,2′,6′-tri-N-(2,2,2-trichloroethoxycarbonyl) gentamicin C$_1$ a in 50 ml. ethanol. Adjust the solution to pH 7 with 2N sulfuric acid in ethanol, then add 494 mg. sodium borohydride and stir the mixture under argon at 25° C for 3 hours. Destroy the excess hydride by the dropwise addition of acetic acid and evaporate the solution. Dissolve the resulting solid in 50 ml. 10% acetic acid in methanol. Then add 338 mg. powdered zinc and heat the mixture at reflux for 4.5 hours. Filter the mixture and wash with methanol, combine the filtrate and methanol washes and evaporate to dryness and azeotrope with toluene. Dissolve the resultant soid in 10 ml. water and adjust the solution to pH 4 with 2N hydrochloric acid. Evaporate the solution, dissolve the residue in water and pass over Amberlite IRA 401S (OH−) resin. Evaporate the eluate and chromatograph the residue on a silica gel column (160 ×2.5 cm.) using the lower phase of a chloroformmethanol-10% ammonium hydroxide solution (2:1:1) as the eluant. Combine like fractions as determined by thin layer chromatography.

a. Combine the less polar fractions containing 1-desamino-1-hydroxygentamicin C$_{1a}$, concentrate, pass over Amberlite IRA 401S (OH−) resin and lyophilize to obtain 1-desamino-1-hydroxygentamicin C$_{1a}$.

b. Combine the more polar fractions containing 1-desamino-1-epi-hydroxygentamicin C$_{1a}$, concentrate, pass over Amberlite IRA 401S (OH−) resin and lyophilize to obtain 1-desamino-1-epi-hydroxygentamicin C$_{1a}$.

B. 1-Desamino-1-hydroxy and 1-desamino-1-epi-hydroxy-4,6-di-O-(aminoglycosyl)-1,3-diaminocyclitols In a manner similar to the procedures described in Example 7 A1, or 7 A2, react the products of Example 3 B. Isolate each of the resultant products to obtain, respectively:

1-desamino-1-hydroxygentamicin $C_2$ and
1-desamino-1-epi-hydroxygentamicin $C_2$,
1-desamino-1-hydroxygentamicin $C_{2a}$ and
1-desamino-1-epi-hydroxygentamicin $C_{2a}$, and the 5-epi, 5-epi-azido-5-deoxy, 5-epi-amino-5-deoxy analogs of the foregoing and of:
1-desamino-1-hydroxygentamicin $C_{1a}$ and
1-desamino-1-epi-hydroxygentamicin $C_{1a}$.

EXAMPLE 8

A. 1-Desamino-1-Hydroxygentamicin $C_{1a}$ and 1-Desamino-1-Epi-Hydroxygentamicin $C_{1a}$ Dissolve 1.7 gm. of 1-desamino-1-oxo-3,2',6'-tri-N-(2,2,2-trichloroethoxycarbonyl)-3''-N-acetylgentamicin $C_{1a}$ from Example 4A in 50 ml. of methanol and adjust the solution to pH 3 using 2N sulfuric acid. Add 408 mg. sodium cyanoborohydride to the solution and stir at 25° C for 18 hours. Then evaporate the reaction mixture to dryness and take up the residue in 50 ml. 10% acetic acid in methanol. Add 428 mg. powdered zinc to the mixture and reflux for 3 hours. Filter the solution, evaporate the filtrate and azeotrope the resultant residue with toluene. Dissolve the resultant residue in 17 ml. 5% aqueous sodium hydroxide and reflux under argon for 60 hours. Cool the solution and neutralize with Amberlite IRC 50 (H+) resin. Wash the resin with water and then elute with 7% ammonium hydroxide solution. Evaporate the basic eluate to dryness and chromatograph the residue on a silica gel column (160 × 2.5 cm.) using the lower phase of a chloroform-methanol-concentrated ammonium hydroxide solution (2:1:1) as the eluant. Combine like fractions as determined by thin layer chromatography. Utilize the separation procedures of Example 7A 1a and b to obtain 1-desamino-1-hydroxygentamicin $C_{1a}$ and 1-desamino-1-epi-hydroxygentamicin $C_{1a}$.

B. 1-Desamino-1-Hydroxy and 1-Desamino-1-Epi-Hydroxy-4,6-di-O-(aminoglycosyl)-1,3-Diaminocyclitols In a manner similar to the procedure described in Example 8A react the products of Example 4B. Isolate each of the resultant products to obtain, respectively, 1-desamino-1-hydroxy-3',4'-dideoxykanamycin B and 1-desamino-1-epi-hydroxy-3',4'-dideoxykanamycin B, 1-desamino-1-hydroxytobramycin and 1-desamino-1-epi-hydroxytobramycin, 1-desamino-1-hydroxykanamycin A and 1-desamino-1-epi-hydroxykanamycin A, the 5-epi, 5-epi-azido-5-deoxy, 5-epi-amino-5-deoxy analogs of the foregoing and of 1-desamino-1-hydroxygentamicin $C_{1a}$ and 1-desamino-1-epi-hydroxygentamicin $C_{1a}$.

EXAMPLE 9

Acid Addition Salts

A. Sulfate Salts (Sulfuric acid addition salts)

Dissolve 5.0 grams of 1-desamino-1-hydroxysisomicin, or 1-desamino-1-epi-hydroxysisomicin in 25 ml. of water and adjust the pH of the solution to 4.5 with 1N sulfuric acid. Pour into about 300 milliters of methanol with vigorous agitation, continue the agitation for about 10-20 minutes and filter. Wash the precipitate with methanol and dry at about 60° C in vacuo to obtain the corresponding 1-desamino-1-hydroxysisomicin sulfate, or 1-desamino-1-epi-hydroxysisomicin sulfate.

In like manner, the sulfate salt of the compounds of Examples 5A, B, 6B, 7A, B and 8B may also be prepared.

B. Hydrochloride Salts

Dissolve 5.0 grams of 1-desamino-1-hydroxysisomicin, or 1-desamino-1-epi-hydroxysisomicin in 25 milliters of water. Acidify with 2N-hydrochloric acid to pH 5. Lyophilize to obtain the corresponding 1-desamino-1-hydroxysisomicin hydrochloride, or 1-desamino-1-epi-hydroxysisomicin hydrochloride.

In like manner, the hydrochloride salt of the compounds of Examples 5A, B, 6B, 7A, B and 8B may also be prepared.

The present invention includes within its scope pharmaceutical compositions comprising our novel 1-desamino-1-hydroxy and 1-desamino-1-epi-hydroxy derivatives of 4,6-di-O-(aminoglycosyl)-1,3-diaminocyclitols with a compatible, pharmaceutically acceptable carrier, or coating. Also included within our invention is the method of eliciting an antibacterial response in a warm-blooded animal having a susceptible bacterial infection which comprises administering to said animal a non-toxic, antibacterially effective amount of a member selected from the group consisting of a 1-desamino-1-hydroxy and a 1-desamino-1-epi-hydroxy derivative of a 4,6-di-O-(aminoglycosyl)-1,3-diaminocyclitol having antibacterial activity.

As discussed hereinabove, the 1-desamino-1-hydroxy and 1-desamino-1-epi-hydroxy derivatives of 4,6-di-O-(aminoglycosyl)-1,3-diaminocyclitols of this invention and the non-toxic pharmaceutically acceptable acid addition salts thereof and broad spectrum antibacterial agents which, advantageously, exhibit activity against organisms, particularly gram-negative organisms. Thus, the compounds of this invention can be used alone, or in combination with other antibiotic agents to prevent the growth or reduce the number of bacteria in various environments. They may be used, for example, to disinfect laboratory glassware, dental and medical equipment contaminated with *Staphylococcus aureus* or other bacteria. The activity of the 1-desamino-1-hydroxy- and 1-desamino-1-epi-hydroxy-4,6-di-O-(aminoglycosyl)-1,3-diaminocyclitols against gram-negative bacteria renders them useful for combating infections caused by gram-negative organisms, e.g. species of *E. coli*, Klebsiella, Serratia and Pseudomonas. Our compounds, e.g. 1-desamino-1-hydroxysisomicin and 1-desamino-1-epi-hydroxysisomicin have veterinary applications, particularly in the treatment of mastitis in cattle and Salmonella induced diarrhea in domestic animals such as the dog and the cat.

In general, the dosage administered of the 1-desamino 1-hydroxy- and 1-desamino-1-epi hydroxy-4,6-di-O-(aminoglycosyl)-1,3-diaminocyclitols will be dependent upon the age and weight of the animal species being treated, the mode of administration, and the type and severity of bacterial infection being prevented, or reduced.

The 1-desamino-1-hydroxy- and 1-desamino-1-epi-hydroxy-4,6-di-O-(aminoglycosyl)-1,3-diaminocyclitols and the pharmaceutically acceptable acid addition salts thereof may be administered orally. They may also be applied topically in the form of ointments, both hydrophilic and hydrophobic, in the form of lotions which may be aqueous, non-aqueous, or other emulsion type, or in the form of creams. Pharmaceutical carriers useful in the preparation of such formulations will include, for example, such substances as water, oils, fats, waxes, polyesters, polyols and the like.

In general, the topical preparations will contain from about 0.1 to about 3.0 gms. of the compounds of this invention per 100 gms. of ointment, creams, or lotion. The topical preparations are usually applied gently to lesions from about 2 to about 5 times a day.

For oral administration the antibacterials of this invention may be compounded in the form of tablets, capsules, elixers, or the like, or may even be admixed with animal feed. It is in these dosage forms that the antibacterials are most effective for treating bacterial infections of the gastrointestinal tract which infections cause diarrhea.

The antibacterials of this invention may be utilized in liquid form such as solutions, suspensions and the like for otic and opthalmic use and may also be administered parenterally via intramuscular, intravenous, intrasternal and subcutaneous injection. The injectable solution, or suspension will usually be administered at from about 1 mg. to about 15 mgs. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed:

| Tablet | Formulation 1 | | |
|---|---|---|---|
| | 10 mg. Tab. | 25 mg. Tab. | 100 mg. Tab. |
| 1-desamino-1-hydroxy- or 1-desamino-1-epi-hydroxysisomicin | 10.50* mg. | 26.25* mg. | 105.00* mg. |
| Lactose, impalpable powder | 197.50 mg. | 171.25 mg. | 126.00 mg. |
| Corn starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |
| Total | 243.0 mg. | 232.5 mg. | 277 mg. |

*5% excess

Procedure

Prepare a slurry consisting of the 1-deamino-1-hydroxy or 1-desamino-1-epi-hydroxysisomicin, lactose and polyvinylpyrrolidone. Spray dry the slurry. Add the corn starch and magnesium stearate. Mix and compress into tablets on a suitable press to the specified weight.

| Formulation 2 | |
|---|---|
| Ointment | |
| 1-deamino-1-hydroxy-, or 1-desamino-epi-hydroxysisomicin | 1.0 gm. |
| Methyl paraben USP | 0.5 gm. |
| Propyl paraben USP | 0.1 gm. |
| Petrolatum | to 1000 gm. |

Procedure

1. Melt the petrolatum.
2. Mix the 1-desamino-1-hydroxy-, or 1-desamino-1-epihydroxysisomicin, methyl paraben and propyl paraben with about 10% of molten petrolatum and make a slurry. Mill the slurry and add to the balance of the petrolatum. Cool to room temperature with agitation.

We claim:

1. A compound selected from the group consisting of a 1-desamino-1-hydroxy derivative and a 1-desamino-1-epi-hydroxy derivative of a 4,6-di-O-(aminoglycosyl)-1,3-diaminocyclitol having antibacterial activity; and the pharmaceutically acceptable acid addition salts thereof.

2. A compound of claim 1 wherein said 6-O-aminoglycosyl is 6-O-garosaminyl.

3. A compound of claim 2 wherein said compound is a 1-desamino-1-hydroxy derivative, or a 1-desamino-1-epi-hydroxy derivative of a 4-O-aminoglycosyl-6-O-garosaminyl-1,3-diaminocyclitol selected from the group consisting of:
Gentamicin B,
Gentamicin $B_1$,
Gentamicin $C_1$,
Gentamicin $C_1a$,
Gentamicin $C_2$,
Gentamicin $C_2a$,
Gentamicin $C_2b$,
Gentamicin $X_2$,
Sisomicin,
Verdamicin,
Antibiotic G-418,
Antibiotic JI-20A,
Antibiotic JI-20B,
Antibiotic G-52,
   the 5-epi, 5-epi-azido-5-deoxy, 5-epi-amino-5-deoxy analogs of the foregoing; and
Antibiotic Mu-1,
Antibiotic Mu-2,
Antibiotic Mu-4 and
Antibiotic Mu-5.

4. A compound of claim 3 which is 1-desamino-1-hydroxygentamicin $C_1$.

5. A compound of claim 3 which is 1-desamino-1-epi-hydroxygentamicin $C_1$.

6. A compound of claim 3 which is 1-desamino-1-hydroxygentamicin $C_1a$.

7. A compound of claim 3 which is 1-desamino-1-epi-hydroxygentamicin $C_1a$.

8. A compound of claim 3 which is 1-desamino-1-hydroxysisomicin.

9. A compound of claim 3 which is 1-desamino-1-epi-hydroxysisomicin.

10. A 1-desamino-1-oxo derivative of a 4,6-di-O-(aminoglycosyl)-1,3-diaminocyclitol selected from the group consisting of:
1-desamino-1-oxo-3,2'-di-N-R-gentamicin A,
1-desamino-1-oxo-3,6'-di-N-R-gentamicin B,
1-desamino-1-oxo-3,6'-di-N-R-gentamicin $B_1$,
1-desamino-1-oxo-3,2'-di-N-R-gentamicin $C_1$, 1-desamino-1-oxo-3,2',6'-tri-N-R-gentamicin $C_{1a}$,
1-desamino-1-oxo-3,2',6'-tri-N-R-gentamicin $C_2$,
1-desamino-1-oxo-3,2',6'-tri-N-R-gentamicin $C_{2a}$,
1-desamino-1-oxo-3,2',-di-N-R-gentamicin $C_{2b}$,
1-desamino-1-oxo-3,2'-di-N-R-gentamicin $X_2$,
1-desamino-1-oxo-3,6',3''-tri-N-R-kanamycin A,
1-desamino-1-oxo-3,2',6',3''-tetra-N-R-kanamycin B,
1-desamino-1-oxo-3,2',6',3'''-tetra-N-R-3',4'-dideoxykanamycin B,
1-desamino-1-oxo-3,2',6'-tri-N-R-sisomicin,
1-desamino-1-oxo-3,2',6',3'''-tetra-N-R-tobramycin,
1-desamino-1-oxo-3,2',6'-tri-N-R-verdamicin,
1-desamino-1-oxo-3,2',6'-tri-N-R-Antibiotic JI-20A,
1-desamino-1-oxo-3,2',6'-tri-N-R-Antibiotic JI-20B,
1-desamino-1-oxo-3,2'-di-N-R-Antibiotic G-52,
1-desamino-1-oxo-3,2'-di-N-R-Antibiotic G-418,
1-desamino-1-oxo-3,2',6'-tri-N-R-Antibiotic 66-40B,
1-desamino-1-oxo-3,2',6'-tri-N-R-Antibiotic 66-40D,
the 5-epi, 5-epi-azido-5-deoxy, 5-epi-amino-5-deoxy analogs of the foregoing; and
1-desamino-1-oxo-3,2',6'-tri-N-R-Antibiotic Mu-1,
1-desamino-1-oxo-3,2',6'-tri-N-R-Antibiotic Mu-2,
1-desamino-1-oxo-3,2',6'-tri-N-R-Antibiotic Mu-4, and
1-desamino-1-oxo-3,5,2',6'-tetra-N-R-Antibiotic Mu-5;
wherein R is an amino protecting group.

11. A compound of claim 10 wherein the amino protecting group is acetyl, trifluoroacetyl, trichloroethoxycarbony, benzoyl, benzyloxycarbonyl, or ethoxycarbonyl.

12. A compound of claim 11 which is 1-desamino-1-3,2'-di-N-trifluoroacetylgentamicin $C_1$.

13. A compound of claim 11 which is 1-desamino-1-oxo-3,2'-6'-tri-N-trichloroethoxycarbonylgentamicin $C_{1a}$.

14. A compound of claim 11 which is 1-desamino-1-oxo-3,2',6'-tri-N-acetylsisomicin.

15. The process for the preparation of a compound selected from the group consisting of a 1-desamino-1-hydroxy, or a 1-desamino-1-epi-hydroxy derivative of a 4,6-di-O-(aminoglycosyl)-1,3-diaminocyclitol, which comprises reaction of a 4,6-di-O-(aminoglycosyl)-1,3-diaminocyclitol having an unsubstituted primary amine at position 1 and all other primary amines protected with an amino protecting group, with an oxidizing agent selected from the group consisting of 3,5-di-t-butyl-1,2-benzoquinone, mesitylglyoxal, 3-nitro-mesitylglyoxal, 3,5-dinitromesitylglyoxal, benzothiazole-2-carbaldehyde, 6-nitrobenzothiazole-2-carbaldehyde and 2-pyridine carboxaldehyde;

followed by reaction in situ of the thereby formed 1-imine intermediate with acid in the range of pH 1-5; then reaction of the thereby formed poly-N-R-1-desamino-1-oxo-4,6-di-O-(aminoglycosyl)-1,3-diaminocyclitol with a hydride donor reducing agent selected from the group consisting of sodium cyanoborohyride, sodium borohydride, morpholinoborane, N,N-diethylanilinoborane, 9-BBN ®, diborane, K-selectride ® and L-selectride ®;

followed by the removal of the amino protecting groups in the thereby formed product mixture comprising poly-N-R-1-desamino-1-hydroxy-4,6-di-O-(aminoglycosyl)-1,3-diaminocyclitol and poly-N-R-1-desamino-1-epi-hydroxy-4,6-di-O-(aminoglycosyl)-1,3-diaminocyclitol; wherein R is an amino protecting group.

16. The process of claim 15 wherein the amino protecting group is acetyl, trifluoroacetyl, trichloroethoxycarbony, benzoyl, benzyloxycarbonyl, 17. The process of claim 15 including the step of isolating the 1-desamino-1-hydroxy-4,6-di-O-(aminoglycosyl)-1,3-diaminocyclitol thereby formed.

18. The process of claim 15 including the step of isolating the 1-desamino-1-epi-hydroxy-4,6-di-O-(aminoglycosyl)-1,3-diaminocyclitol thereby formed.

19. The method of eliciting an antibacterial response in a warm-blooded animal having a susceptible bacterial infection which comprises administering to said animal a non-toxic antibacterially effective amount of a member selected from the group consisting of a 1-desamino-1-hydroxy and a 1-desamino-1-epihydroxy analog of a 4,6-di-O-(aminoglycosyl)-1,3-diaminocyclitol having antibacterial activity;

and the pharmaceutically acceptable acid addition salts thereof.

20. A pharmaceutical composition comprising an antibacterially effective amount of a compound selected from the group consisting of a 1-desamino-1-hydroxy and a 1-desamino-1-epihydroxy analog of a 4,6-di-O-(aminoglycosyl)-1,3-diaminocyclitol having antibacterial activity;

and the pharmaceutically acceptable acid addition salts thereof;

together with a non-toxic pharmaceutically acceptable carrier.

* * * * *

UNITED STATES PATENT OFFICE
CERTIFICATE OF CORRECTION

Patent No. 4,066,752          Dated January 3, 1978

Inventor(s) Alan K. Mallams et al

It is certified that error appears in the above-identified patent and that said Letters Patent are hereby corrected as shown below:

Title, first page, "1-Desamino-1-Hydroxy and 1-Desamino-1-Epi-Hydroxy-4,6-Di-O-(Aminoglycosyl)-1,3-Diaminocyclitols: 1-Desamino-1-Oxo-4,6-Di-O-(Aminoglycosyl)-1,3-Diaminocyclitols, Intermediates and Use as Antibacterial Agents" should read ---1-Desamino-1-Hydroxy and 1-Desamino-1-Epi-Hydroxy-4,6-Di-O-(Aminoglycosyl)-1,3-Diaminocyclitols, Methods for their Manufacture and Novel 1-Desamino-1-Oxo-4,6-Di-O-(Aminoglycosyl)-1,3-Diaminocyclitols, Intermediates Useful Therein, Methods for their Use as Antibacterial Agents and Compositions Useful Therefor---. Column 1, Title, "1-Desamino-1-Hydroxy and 1-Desamino-1-Epi-Hydroxy-4,6-Di-O-(Aminoglycosyl)-1,3-Diaminocyclitols: 1-Desamino-1-Oxo-4,6-Di-O-(Aminoglycosyl)-1,3-Diaminocyclitols, Intermediates and Use as Antibacterial Agents" should read ---1-Desamino-1-Hydroxy and 1-Desamino-1-Epi-Hydroxy-4,6-Di-O-(Aminoglycosyl)-1,3-Diaminocyclitols, Methods for their Manufacture and Novel 1-Desamino-1-Oxo-4,6-Di-O-(Aminoglycosyl)-1,3-Diaminocyclitols, Intermediates Useful Therein, Methods for their Use as Antibacterial Agents and Compositions Useful Therefor---. Column 5, line 26, "-4,69-di-O-" should read ---4,6-di-O---. Column 6, line 52, "Antibiotic G-148" should read ---Antibiotic G-418---; line 60, "-3,4'-di-N-trifluoroacetylgentamicin $B_1$," should read ---3,6'-di-N-trifluoroacetylgentamicin $B_1$,---. Column 8, line 25, "1.4 (3H, broad s," should

UNITED STATES PATENT OFFICE
CERTIFICATE OF CORRECTION

Patent No. 4,066,752     Dated January 3, 1978

Inventor(s) Alan K. Mallams et al

It is certified that error appears in the above-identified patent and that said Letters Patent are hereby corrected as shown below:

read ---1.14 (3H, broad s,---.  Column 9, line 19, "3'-N-acetyl-" should read ---3"-N-acetyl---.  Column 13, line 16, "ppm. ($C_2$'); and" should read ---ppm. ($C_1$'); and---.  Column 20, line 22, Claim 16, "ycarbony, benzoyl, benzyloxycarbonyl," should read --ycarbonyl, benzoyl, benzyloxycarbonyl, or ethoxycarbonyl.---.

Signed and Sealed this

Sixth Day of February 1979

[SEAL]

Attest:

RUTH C. MASON
Attesting Officer

DONALD W. BANNER
Commissioner of Patents and Trademarks